US010953122B2

(12) United States Patent
Dudley (10) Patent No.: US 10,953,122 B2
(45) Date of Patent: *Mar. 23, 2021

(54) SEALABLE DECONTAMINATION HOLDING VESSEL FOR ISOLATING CONTAMINATED ITEMS

(71) Applicant: Safe-Decon, Inc., Titusville, FL (US)

(72) Inventor: Bobbie E. Dudley, Titusville, FL (US)

(73) Assignee: Safe-Decon, Inc., Titusville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/126,591

(22) Filed: Sep. 10, 2018

(65) Prior Publication Data

US 2019/0015538 A1 Jan. 17, 2019

Related U.S. Application Data

(63) Continuation of application No. 14/947,681, filed on Nov. 20, 2015, now Pat. No. 10,071,178.

(60) Provisional application No. 62/097,966, filed on Dec. 30, 2014.

(51) Int. Cl.
| H05B 6/64 | (2006.01) |
| A61L 2/26 | (2006.01) |
| A61L 2/07 | (2006.01) |
| A61L 2/28 | (2006.01) |

(52) U.S. Cl.
CPC ........ *A61L 2/26* (2013.01); *A61L 2/07* (2013.01); *A61L 2/28* (2013.01); *A61L 2202/122* (2013.01)

(58) Field of Classification Search
CPC ........ B65D 26/16; B65D 47/32; B65D 53/02; B65F 1/06; B65F 1/08; A61L 2/26; A61L 2/28; A61L 2/07; A61L 2202/122

USPC .......... 220/495.11, 23.83, 23.87, 23.89, 501, 220/528, 908, 908.1, 495.04, 49, 5.06, 220/495.08, 495.06; 422/300; 53/425

See application file for complete search history.

(56) References Cited

U.S. PATENT DOCUMENTS

| 2,384,398 A | 11/1943 | Andersen et al. |
| 4,662,516 A | 5/1987 | Baker, Sr. et al. |
| 4,670,227 A | 6/1987 | Smith |
| 4,798,292 A | 1/1989 | Hauze |
| 5,117,997 A | 6/1992 | Fink |
| 5,124,126 A | 6/1992 | Ripp |
| 5,385,102 A | 1/1995 | Withers, Jr. et al. |

(Continued)

*Primary Examiner* — James N Smalley
*Assistant Examiner* — Elizabeth J Volz
(74) *Attorney, Agent, or Firm* — Wiggin and Dana LLP; Gregory S. Rosenblatt; Thomas M. Landman (57) ABSTRACT

A sealable decontamination holding vessel configured to isolate contaminated items being held therein until safe opening of the vessel occurs during a high pressure and temperature sterilization cycle in an autoclave. The vessel basically includes an outer container, a perforated inner receptacle, containment bag and cover lid. The inner receptacle fits into the outer container. The containment bag fits within the inner receptacle with an open end of the bag draped over an open top lip of the inner receptacle. The cover lid is secured and sealed over the open top of the outer container. Patches of self-adhering sealing materials are placed over vent holes in the outer container and cover lid so as to seal the same until they unseal in response to contact with sterilizing steam in the autoclave allowing flow of the steam through the outer container into the inner receptacle and containment bag.

10 Claims, 6 Drawing Sheets

(56) References Cited

U.S. PATENT DOCUMENTS

| | | |
|---|---|---|
| 5,523,519 A | 6/1996 | Weber et al. |
| 6,589,477 B1 | 7/2003 | Frieze et al. |
| 6,626,321 B2 * | 9/2003 | Jaeger ................... B65F 1/04 220/23.87 |
| 7,210,596 B1 | 5/2007 | Ruccolo |
| 8,567,338 B2 | 10/2013 | Greene et al. |
| 10,071,178 B2 * | 9/2018 | Dudley, Jr. ............. A61L 2/26 |
| 2003/0185731 A1 | 10/2003 | Wu et al. |
| 2004/0206760 A1 | 10/2004 | Gagnebin |
| 2011/0024430 A1 | 2/2011 | Meissen et al. |
| 2011/0100997 A1 * | 5/2011 | Gagnebin ............... B65F 1/06 220/495.04 |
| 2014/0042167 A1 * | 2/2014 | Lindsay ................. A47J 36/10 220/361 |

* cited by examiner

SEALABLE DECONTAMINATION HOLDING VESSEL FOR ISOLATING CONTAMINATED ITEMS

CROSS REFERENCE(S) TO RELATED APPLICATION(S)

This application is a continuation patent application of U.S. patent application Ser. No. 14/947,681, filed Nov. 20, 2015, which claims the benefit of U.S. Provisional Patent Application Ser. No. 62/097,966, filed Dec. 30, 2014, which is hereby incorporated in its entirety herein.

FIELD OF THE INVENTION

The present invention relates to safe decontamination of contaminated items and, more particularly, is concerned with a sealable decontamination holding vessel for isolating contaminated items until safe opening of the vessel occurs during a high pressure and temperature steam sterilization cycle in an autoclave.

BACKGROUND OF THE INVENTION

Bio-research institutes have problems in safely transporting airborne pathogens from under hoods and into an autoclave without exposing people to aerosols from open containers. Hospitals dealing with people in isolation have problems with limiting exposure to, and safe sterilization of, their contaminated clothing, needles, trash and other items. Contaminated items have to be sealed until they are ready to be transferred for introduction into an autoclave. Once at the autoclave, the bags holding contaminated items are opened in order to transfer the contaminated items to the autoclave. Unfortunately, this conventional process enables aerosols to potentially contaminate individuals handling the bags and other individuals exposed to the aerosols.

Accordingly, there remains a need in the art for an innovation that will overcome the drawbacks, disadvantages and limitations of conventional approaches to the aforementioned problems.

SUMMARY OF THE INVENTION

The present invention is directed to an innovation that overcomes the deficiencies of the past approaches and the problems that remain unsolved, through the provision of a sealable decontamination holding vessel for isolating contaminated items until safe opening of the vessel occurs during a high pressure and temperature steam sterilization cycle in an autoclave.

In one aspect of the present invention, a sealable decontamination holding vessel for isolating contaminated items, the vessel including:

- an outer container having an open top and an interior holding chamber;
- an inner receptacle having an open top and an interior confining chamber, the inner receptacle fitting through the open top of the outer container and into the interior holding chamber of the outer container so as to provide a void between the outer container and the inner receptacle;
- a containment bag having a top open end and an interior collection cavity, the containment bag fitting through the open top of the inner receptacle and into the interior confining chamber of the inner receptacle such that the top open end of the containment bag drapes over the open top of the inner receptacle;
- a cover lid securable and sealable over and upon the open top of the outer container; and
- a plurality of vents in at least one of the outer container and the cover lid being configured to allow flow of sterilizing steam in an autoclave through the vents and into the inner receptacle and containment bag and into contact with contaminated items in the interior collection cavity of the containment bag.

In another aspect of the present invention, a sealable decontamination holding vessel for isolating contaminated items, the vessel including:

- an outer container including
  - a continuous side wall with an open top,
  - a bottom end wall enclosing a bottom of said side wall, the bottom end wall and the side wall being made of a rigid material and defining an interior holding chamber being open at a top of the side wall, and
  - a plurality of spacers affixed to and extending vertically along an inside surface of the side wall from the bottom wall to short of the open top of the side wall,
  - wherein the side wall also has a first plurality of vents formed therethrough at least at one of spaced locations about the side wall between and spaced from the spacers and spaced locations on the bottom wall;
- an inner receptacle including
  - a continuous side wall, and
  - a bottom end wall enclosing a bottom of the side wall of the inner receptacle, the bottom end wall and the side wall of the inner receptacle being made of a rigid material and defining an interior confining chamber being open at a top of the side wall of the inner receptacle,
  - wherein the inner receptacle is adapted to insert through the open top of the side wall of the outer container, into the interior holding chamber of the outer container so as to fit within an inner space whose perimeter is defined by inner edges of the spacers affixed to the inside surface of the side wall of the outer container so as to leave an outer void extending between the spacers and about the inner receptacle and in communication with the first plurality of vents;
- a container bag made of a flexible material and having an open end, the containment bag defining an interior collection cavity being accessible through the open end thereof for depositing contaminated items therein, wherein the bag is adapted to insert through the open top of the inner receptacle into the interior confining chamber thereof and at the open end of the bag to drape over and about the open top of the side wall of the inner receptacle for suspending the bag in the interior confining chamber of the inner receptacle; and
- a lid cover made of a rigid material and having a central panel and an annular outer skirt surrounding and attached with a periphery of the central panel, the lid cover at the central panel having a second plurality of vents formed therethrough at spaced locations on the central panel, the lid cover at the periphery thereof being placeable upon the open top of the side wall of the outer container such that the lid cover at the annular outer skirt thereof extends thereabout so as to cover the open top of the outer container and such that the lid cover between the central panel of the lid cover and the open end of the containment bag draped over and about the open top end of the inner receptacle creates a gap that provides communication between the outer void and the interior collection cavity of the containment bag.

In still another aspect of the present invention, a sealable decontamination holding vessel for isolating contaminated items includes:

an outer container having an open top, an interior holding chamber, a plurality of spacers affixed to and extending vertically along an inside surface of the outer container, and a first plurality of vents communicating the exterior of the outer container with the interior holding chamber at locations between the spacers;

an inner receptacle having an open top, an interior confining chamber, and a multiplicity of perforations communicating the interior confining chamber with the interior holding chamber of the outer container, the inner receptacle being configured to be inserted through the open top of the inner receptacle and into the interior holding chamber of the outer container to within a central volume of the interior holding chamber, whose perimeter is defined by inner edges of the spacers affixed to the inside surface of the outer container, in which the inner receptacle assumes a freestanding upright orientation upon the inside surface at a bottom of the outer container so as to leave a void extending between the spacers and about the inner receptacle located in the central volume;

a containment bag having an open end and an interior collection cavity accessible through the open end for depositing contaminated items therein, the bag being configured to insert through the open top of the inner receptacle into the interior confining chamber thereof and at the open end of the bag to overlap or drape over and about the open top of the inner receptacle for suspending the bag in the interior confining chamber of the inner receptacle;

a cover lid configured to cover and be sealably secured upon the open top of the outer container so as to leave a gap between the cover lid and the open end of the containment bag, the cover lid having a second plurality of vents at spaced locations on the cover lid communicating the exterior of the cover lid with the interior holding and confining chambers of the outer container and inner receptacle; and first and second pluralities of patches of self-adhering sealing materials mountable over the respective first and second pluralities of vents so as to seal the same, the patches being configured to unseal in response to contact with sterilizing steam, thereby allowing sterilizing steam into the interior holding chamber of the outer container, through the void between the spacers and around the inner receptacle, through the perforations into the interior confining chamber of the inner receptacle, and through the gap between the cover lid and open end of the containment bag and into contact with the contaminated items in the bag.

In another aspect of the present invention, the holding vessel also includes a plurality of securement devices anchored to one of the outer container adjacent to the open top thereof and the cover lid adjacent to an outer periphery thereof, and configured to engage the other of the outer container and cover lid in order to secure the cover lid upon the outer container.

In another aspect of the present invention, the holding vessel further includes an annular gasket constructed of a yieldable resilient material, configured for being seated upon an annular outwardly protruding rim on the open top of the outer container, to form an annular seal between the cover lid and open top of the outer container when the cover lid is secured upon the outer container.

In another aspect of the present invention, the holding vessel still further includes a probe hole, or aperture, defined through the outer container and configured to receive a probe extendable from a location exterior of the outer container, through the probe hole, into the interior holding chamber of the outer container.

In another aspect of the present invention, the holding vessel yet further includes a probe aperture defined through the inner receptacle at a location enabling alignment with the probe hole in the outer container, to receive a portion of the probe extendable from a location exterior of the inner receptacle, through the probe aperture, into the interior holding chamber of the inner receptacle.

These and other aspects, features, and advantages of the present invention will become more readily apparent from the attached drawings and the detailed description of the preferred embodiments, which follow.

BRIEF DESCRIPTION OF THE DRAWINGS

The preferred implementations of the invention will hereinafter be described in conjunction with the appended drawings, provided to illustrate and not to limit the invention, in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Referring now to FIGS. 1-4 and 7, there is illustrated an exemplary implementation of a sealable decontamination holding vessel, generally designated 100, for isolating contaminated items in accordance with aspects of the present invention. The vessel 100 is adapted to isolate the contaminated items being held therein until safe opening of the vessel occurs during a high pressure and temperature sterilization cycle in an autoclave (not shown). The sealable holding vessel 100 basically includes an outer container 102, an inner receptacle 104, a containment bag 106, and a cover lid 108.

The outer container 102 of the vessel 100 has a continuous side wall 110 and a bottom end wall 112 enclosing a bottom of the side wall 110. In addition, the outer container 102 has a plurality of spacers 114 affixed to and extending vertically along an inside surface 110A of the side wall 110 from the bottom end wall 112 to short of an annular outwardly protruding top rim 110B defining an open top of the side wall 110. The side wall 110, by way of example but not limitation, may have a cylindrical configuration. At its bottom, the side wall 110 merges or integrally connects with the periphery of the bottom end wall 112. The outer container 102 and the lid cover 108 may be made of the same material, such as a suitable metal or a suitable plastic, such as polypropylene by way of example but not limitation. The side wall 110 and the bottom end wall 112 together define an interior holding chamber 116 open at the open top of the side wall 110.

The side wall 110 of the outer container 102 has a probe hole 118 defined through the side wall 110 at a location spaced intermediately between the bottom end wall 112 and the top rim 110B of the side wall 110. The probe hole 118 is configured to receive a conventional monitoring probe (not shown) being extendable from the exterior of the outer container 102 of the vessel 100, through the probe hole 118, into the interior holding chamber 116 of the outer container 102. The side wall 110 of the outer container 102 further has a first plurality of vents 120 defined through the side wall 110, such as at locations spaced apart approximately ninety degrees, by way of example but not limitation, so as to communicate the exterior of the outer container 102 with the interior holding chamber 116 at locations between the spacers 114. The purpose served by the first plurality of vents 120 will be explained hereinafter.

Figure 3:
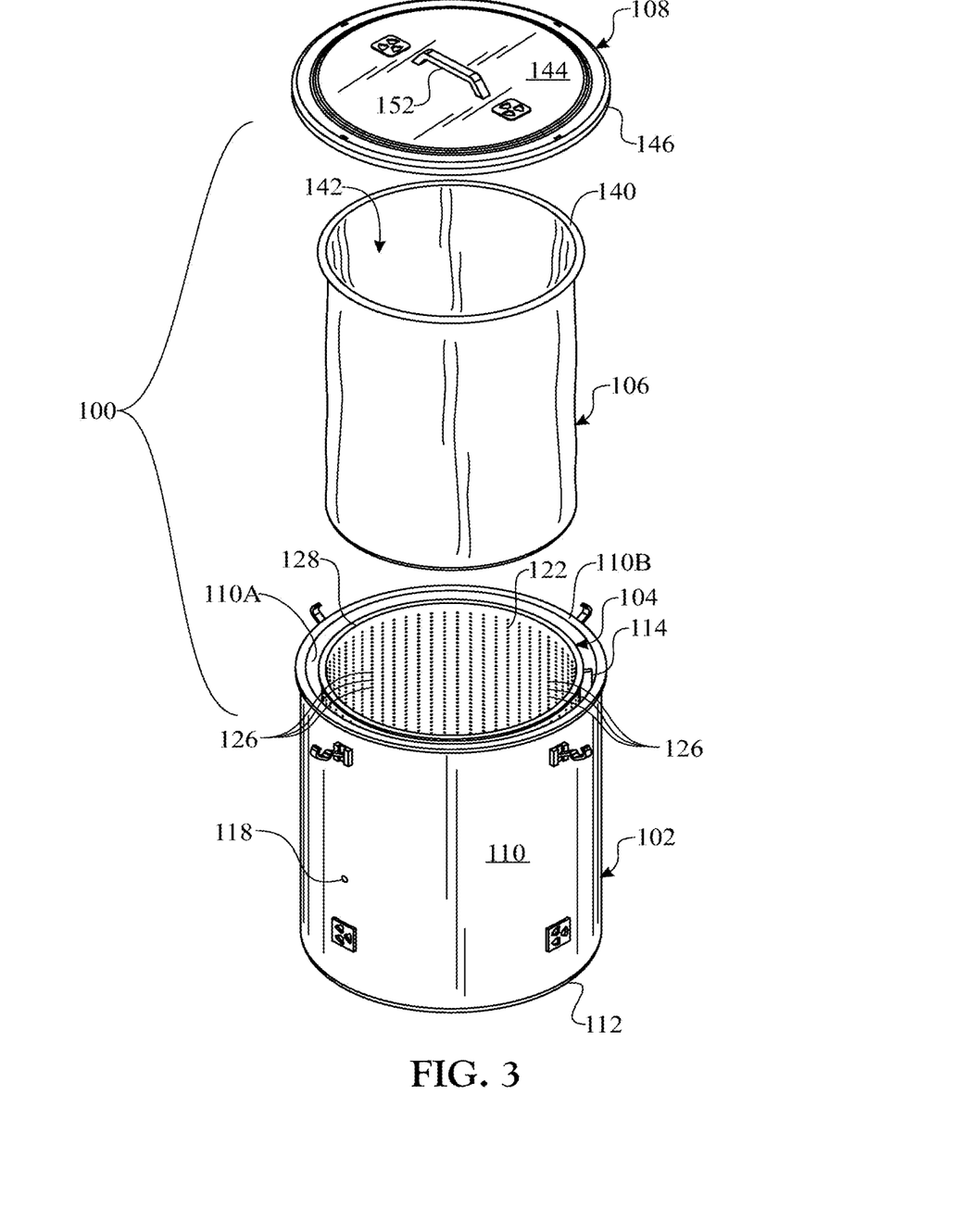
FIG. 3 presents an upper partially-exploded isometric view of the vessel originally introduced in FIG. 1, showing, in addition to the lid cover being removed, the containment bag removed from the perforated inner receptacle still disposed within the outer container of the vessel.
Figure 4:
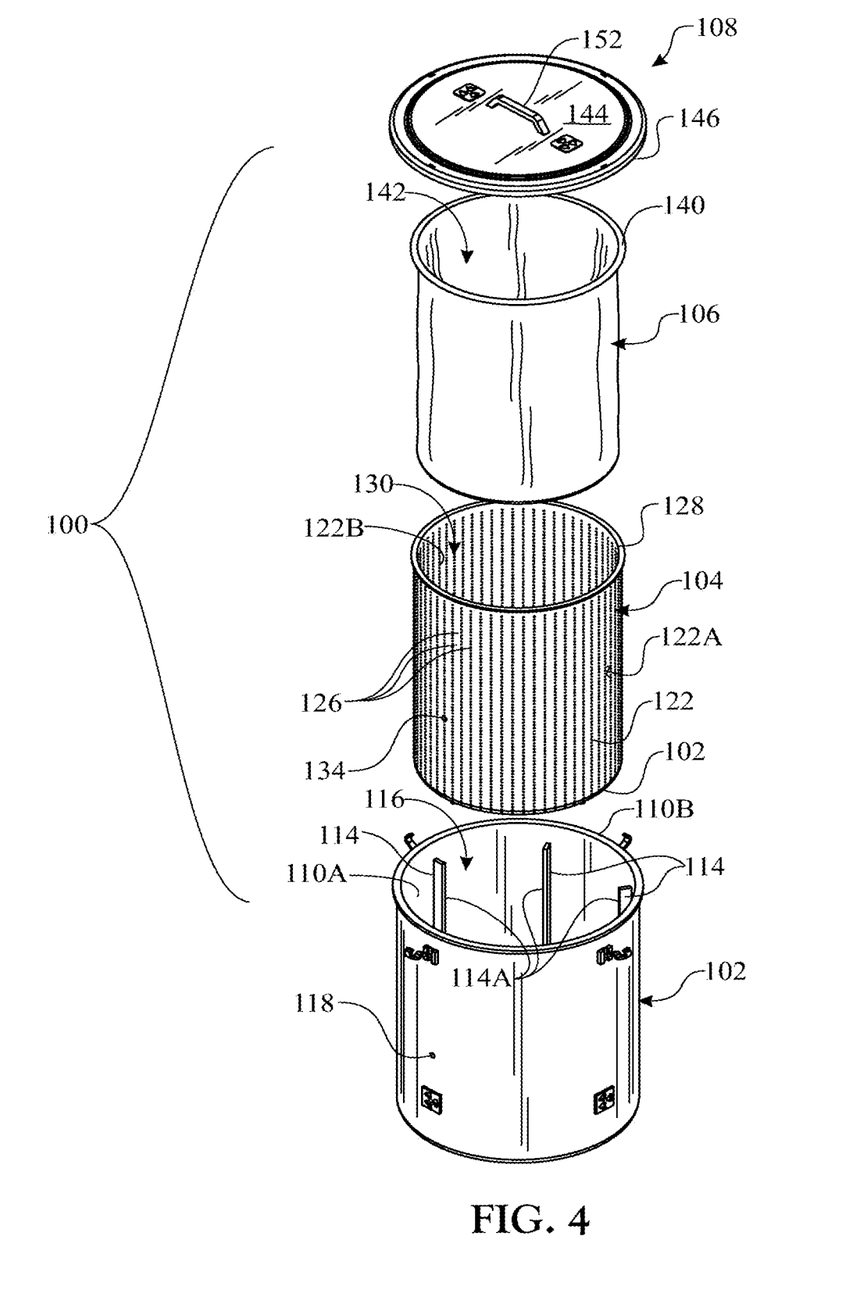
FIG. 4 presents an upper fully-exploded isometric view of the vessel originally introduced in FIG. 1, showing, in addition to the lid cover and containment bag being removed, the perforated inner receptacle removed from the outer container of the vessel.
Figure 7:
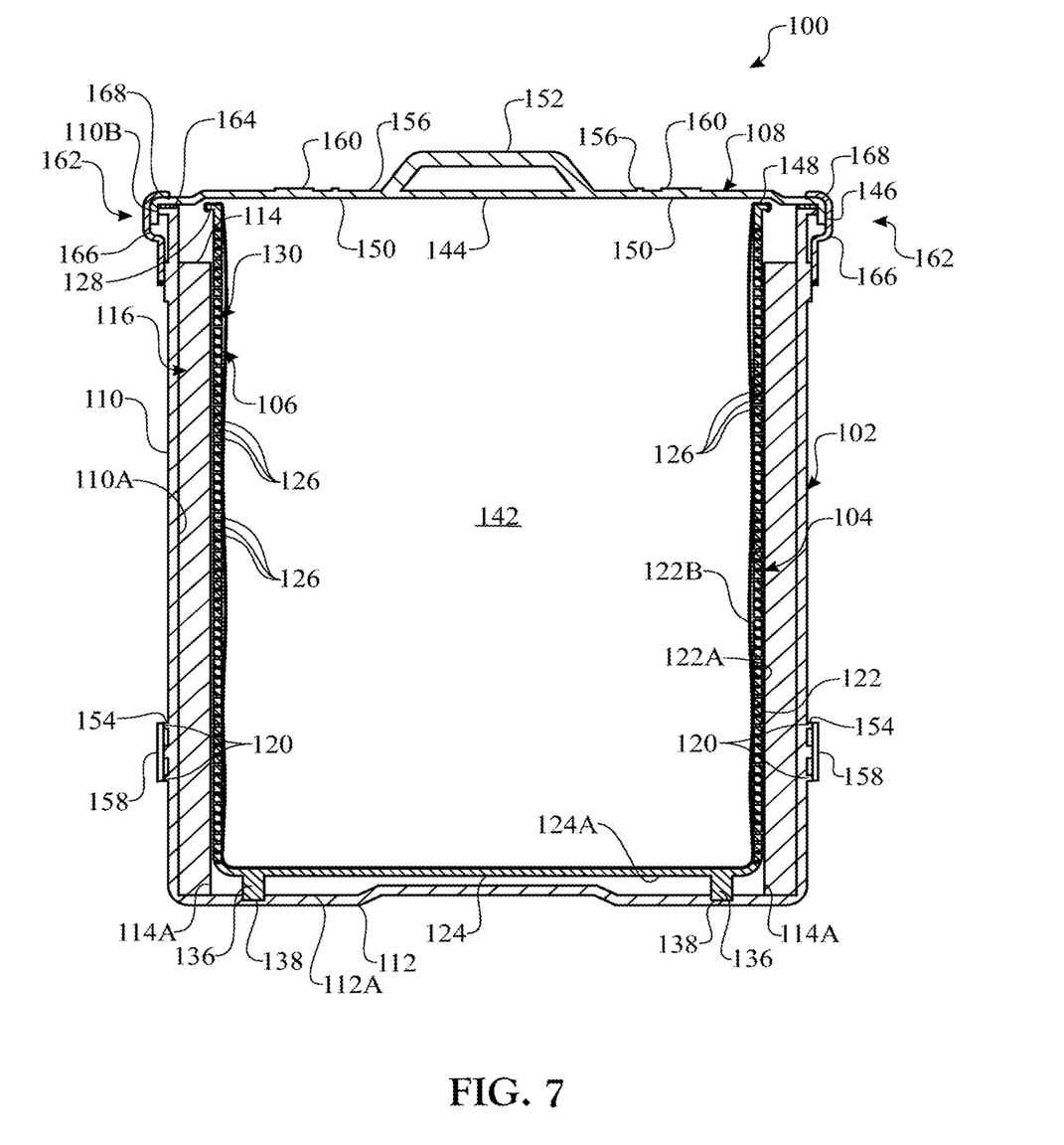
FIG. 7 presents a longitudinal sectional view of the vessel taken along sectional line 7-7 of FIG. 5.

The inner receptacle 104 of the vessel 100 has a continuous side wall 122 and a bottom end wall 124 enclosing a bottom of the side wall 122. In addition, the inner receptacle 104 has a multiplicity, or plurality, of perforations 126, preferably uniformly spaced about, and provided through, the side wall 122 between its exterior and interior surfaces, 122A and 122B, respectively, as best seen in FIGS. 3, 4 and 7. The perforations 126 are present from adjacent to the bottom end wall 124 to short of an annular outwardly protruding top lip 128 defining an open top of the side wall 122. At its bottom, the side wall 122 merges or integrally connects with the periphery of the bottom end wall 124. The inner receptacle 104 may be made of a rigid material, such as stainless steel, by way of example but not limitation. The side wall 122 and the bottom end wall 124 together define an interior confining chamber 130, which is open at the open top of the side wall 122. The side wall 122 of the inner receptacle 104 preferably has the same configuration, such as cylindrical, as the outer container 102.

Figure 2:
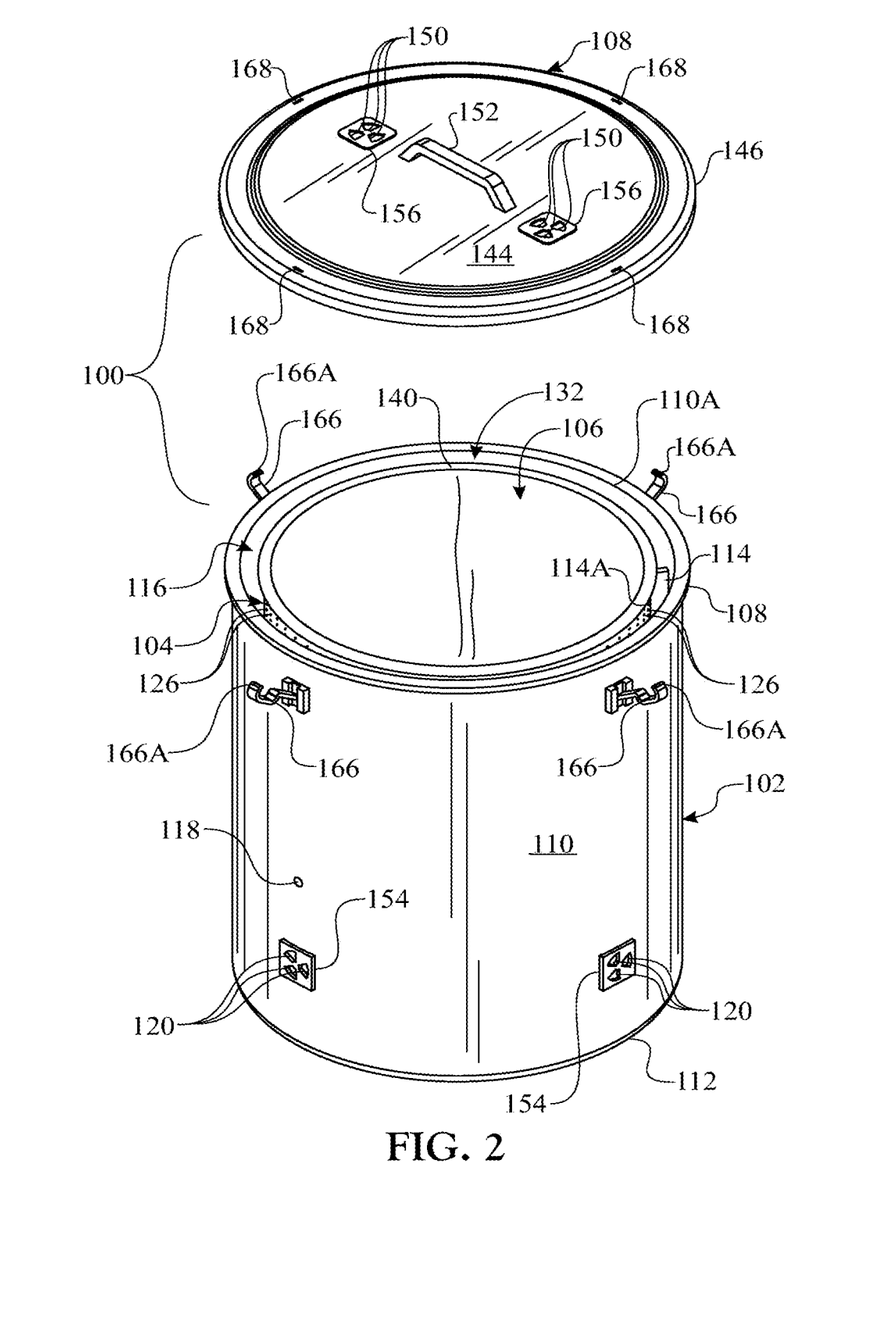
FIG. 2 presents an upper isometric view of the vessel originally introduced in FIG. 1, showing an outer container of the vessel having therein a containment bag nested in a perforated inner receptacle and being opened by removal of a lid cover of the vessel.

Thus, the inner receptacle 104 is configured to insert within and past the annular top lip 128, defining the open top, of the side wall 122 and into the interior holding chamber 116 of the outer container 102, so as to assume a freestanding upright orientation therein upon an inside surface 112A of the bottom end wall 112 of the outer container 102, as seen in FIG. 7. More particularly, the inner receptacle 104 fits within a central volume within the interior holding chamber 116 of the outer container 102. The perimeter of the central volume is defined by and between inner edges 114A on the spaced-apart vertical spacers 114, such as five spacers, by way of example but not limitation, affixed on the inside surface 110A of the side wall 110 of the outer container 102. This arrangement leaves a void 132, as best seen in FIG. 2, extending between each adjacent pair of spacers 114 and about the inner receptacle 104 located in the central volume of the interior holding chamber 116, from the interior surface 110A of the outer container 102 to the exterior surface 122A of the inner receptacle 104.

The side wall 122 of the inner receptacle 104 has a probe aperture 134 defined through the side wall 122 at a location spaced intermediately between the bottom end wall 124 and the top lip 128 of the side wall 122 of the inner receptacle 104. The probe aperture 134 in the side wall 122 of the inner receptacle 104 is alignable with the probe hole 118 in the side wall 110 of the outer container 102, enabling it to receive a portion of the probe from a position exterior of the inner receptacle 104, through the probe aperture 134, into the interior confining chamber 130 of the inner receptacle 104. The bottom end wall 124 of the inner receptacle 104 may have a plurality of spaced-apart feet 136 provided on and protruding below an exterior surface 124A of the bottom end wall 124. In order to aid in aligning the probe aperture 134 of the inner receptacle 104 with the probe hole 118 of the outer container 102, the feet 136 are configured to seat into a plurality of spaced apart recesses 138 formed in the inside surface 112A of the bottom end wall 112 of the outer container 102 when the probe aperture 134 is aligned with the probe hole 118.

The containment bag 106 of the vessel 100 is made of flexible material such as a suitable plastic material that can withstand the high pressures and temperatures typically used in autoclaves. The bag 106 has an outwardly-flanged open top end 140 and an interior collection cavity 142. The interior collection cavity 142 is accessible through the outwardly-flanged open top end 140 of the bag 106 for depositing contaminated items therein. Preferably, the bag 106 has a size and configuration adapting it to be easily inserted through the open top of the inner receptacle 104, to lie along the interior surfaces 122B, 124B of the side wall 122 and bottom end wall 124 of the inner receptacle 104, and to overlap, or drape over, the top lip 128 at the open top of the side wall 122 of the inner receptacle 104, thereby facilitating suspension of the bag 106 in the interior confining chamber 130 of the inner receptacle 104, as seen in FIG. 7.

Referring to FIGS. 1-7, the cover lid 108 of the vessel 100 has a central panel 144 and an annular outer skirt 146 surrounding and merging from the central panel 144, such that the cover lid 108 at the periphery thereof is configured to cover and be sealably secured upon the open top of the outer container so as to leave a gap 148 between the cover lid 108 and the outwardly-flanged open top end 140 of the containment bag 106. The cover lid 108 has a second plurality of vents 150 defined through the cover lid 108 at spaced locations thereon so as to communicate the exterior of the cover lid 108 with the interior holding and confining chambers, 116 and 130, respectively, of the outer container 102 and inner receptacle 104. Such locations may be spaced-apart approximately 180°, by way of example but not limitation, from one another adjacent to opposite ends of a central handle 152 on the cover lid 108. The purpose served by the second plurality of vents 150 will be explained hereinafter.

The outer container 102 and the cover lid 108 of the vessel 100 respectively have plate-shaped pads 154, 156 affixed to the exteriors thereof at the locations of the first and second pluralities of vents 120, 150 so as to surround the vents 120, 150 and provide areas adapted to place first and second pluralities of seal patches 156, 160 of self-adhering sealing materials, respectively, over the first and second pluralities of vents 120, 150 on the exteriors of the side wall 110 of the outer container 102 and the central panel 144 of the cover lid 108. The seal patches 158, 160 are configured to unseal from the outer container 102 and the cover lid 108 in response to contact with sterilizing steam encountered in an autoclave, thereby allowing sterilizing steam to flow into the interior holding chamber 116 of the outer container 102 and therefrom, through the multiplicity of perforations 126 in the inner receptacle 104, and upwardly through the void 132 between the vertical spacers 114 and about the inner receptacle 104, through the gap 148 between the cover 108 and the outwardly flanged open top end 140 of the containment bag 106, into contact with the contaminated items in the containment bag 106.

Figure 1:
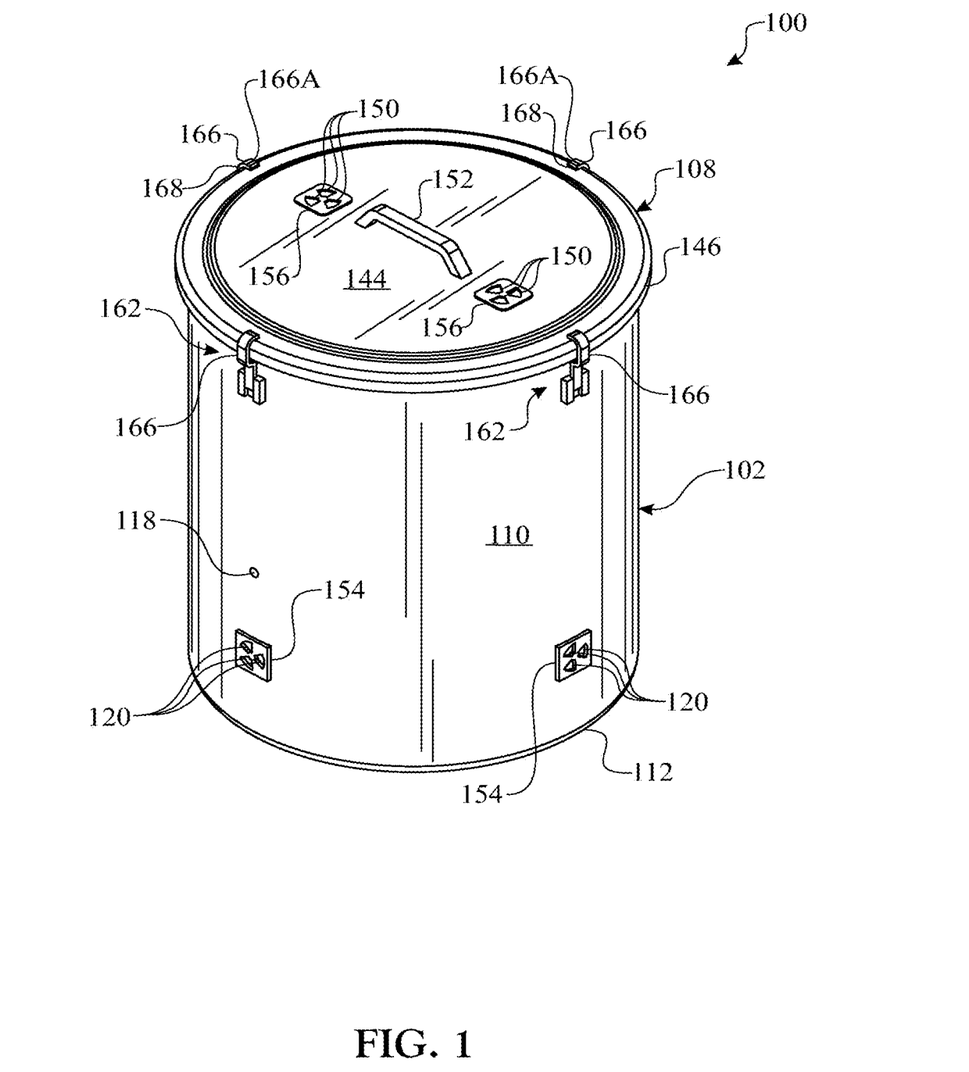
FIG. 1 presents an upper isometric view of an exemplary implementation of a sealable decontamination holding vessel for isolating contaminated items in accordance with aspects of the present invention.
Figure 5:
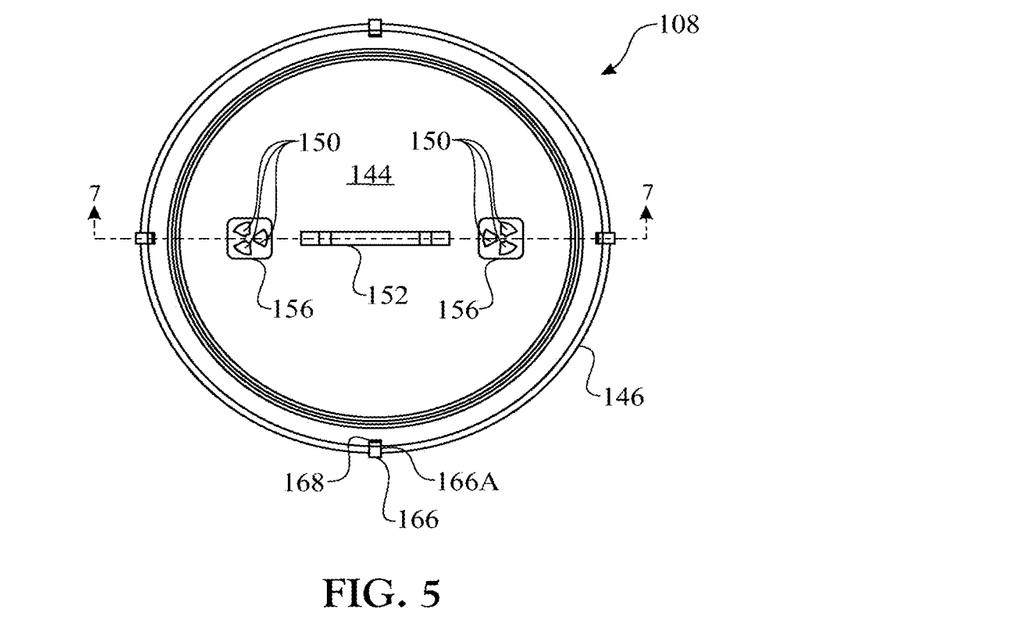
FIG. 5 presents a top plan view of the vessel originally introduced in FIG. 1, showing the vessel after being rotated counterclockwise approximately 45 degrees from its position in FIG. 1.
Figure 6:
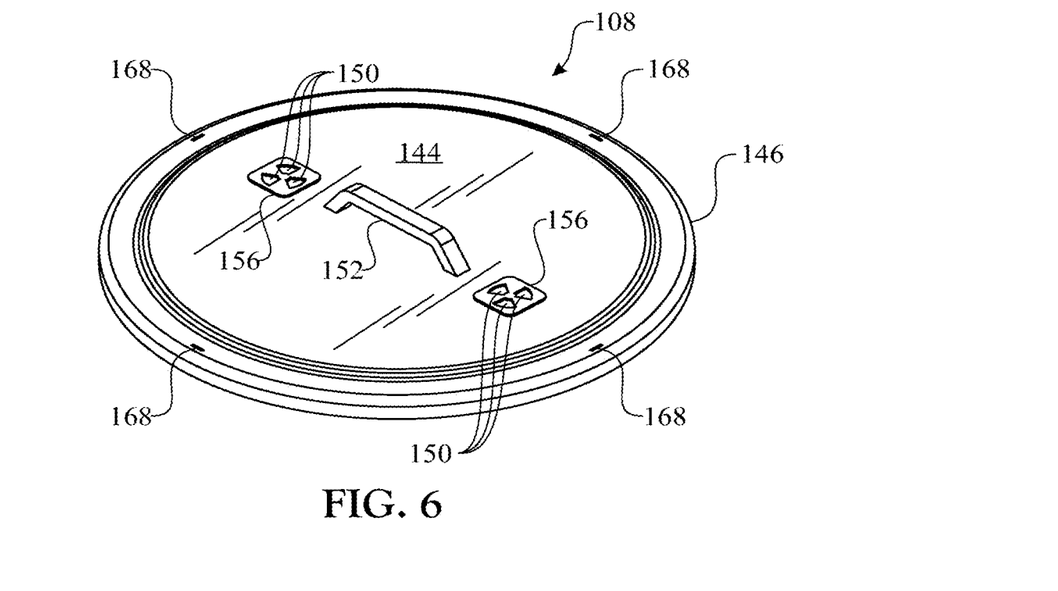
FIG. 6 presents an upper isometric view of the lid cover of the vessel originally introduced in FIG. 1.

The vessel 100 also includes a plurality of securement devices 162 configured to releasably-secure the cover lid 108 upon the outer container 102, and an annular gasket 164, constructed of a yieldable resilient material, located upon the annular outwardly protruding top rim 110B of the side wall 110 of the outer container 102, to provide a seal between the outer container 102 and the cover lid 108 when the securement devices 162 are actuated to secure the cover lid 108 upon the outer container 102. Preferably, the securement devices 162 take the form of spaced-apart latch hooks 166, being conventional well-known types per se, pivotally anchored to the side wall 110 of the outer container 102, at locations spaced below the rim 110B thereof, and a plurality of spaced-apart depressions 168 formed in the periphery of the cover lid 108 inwardly from the outer skirt 146. The spacing between the respective latch hooks 166 and the spacing between the respective depressions 168 are the same, such as 90°, by way of example but not limitation. When the latch hooks 166 are actuated from their unlatching positions, as seen in FIG. 2-4, to their latching positions, as shown in FIGS. 1, 5 and 7, the outer tips 166A of the latch hooks 166 are manipulated to catch in the depressions 168 on the cover lid 108 adjacent to the annular outer skirt 146 thereof, and thereby sealably fasten or secure cover lid 108 upon the outer container 102. It should be noted that in the illustrated embodiment the latch hooks 166 are not in registry with the vertical spacers 114, although alternatively they may be the same both in number and relative position if desired.

In addition, or alternatively, plate-shaped pads may also be affixed to the interiors of the outer container 102 and the cover lid 108 at the locations of the first and second pluralities of vents 120, 150 so as to surround the vents 120, 150 and provide areas adapted to place first and second pluralities of seal patches of self-adhering sealing materials or patches of filter materials over the first and second pluralities of vents 120, 150. Arrangements in these areas of the vessel 100 may different depending upon whether the vessel 100 is to be used in a healthcare environment or a bio-research institute environment. It will be noted that suitable space is provided above the vertical spacers 114 to allow for the presence of a person's fingers to install or remove the inner receptacle 104 and bag 106 supported therein.

After placing the above-described vessel 100 in an autoclave, at approximately 140° F. a purging of the seal patches on the vessel with steam will cause them to open, allowing steam to penetrate and thus sterilization to be carried out through a 250° F. pre-vacuum (also referred to as "prevac") cycle over a 45-minute duration of sterilization. In the healthcare environment, the vessel 100 may be placed in a sink, instead of an autoclave, the outer seal patches removed, the sink drain plugged, and the sink filled with bleach and water until the vessel is covered. After an appropriate time period, the sink is drained and the decontaminated items in the vessel removed and appropriately disposed of. In both healthcare and research institute environments, it is desirable to spray the outside of the vessel with an appropriate decontaminating chemical prior to placement in the sink or autoclave. It will be noted that in both uses, the containment bag remains open at all times. The bag, by way of example but not limitation, may have a capacity of three gallons.

The above-described embodiments are merely exemplary illustrations of one or more implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

For example, it will be apparent to those skilled in the art that alternative usages for the container are possible and contemplated. For instance, to facilitate a sustained release chemical treatment, the container can be immersed in chemically-treated water in a soak sink. In this case, as the water fills the soak tank and treated water enters the container through the bottom apertures, the air will escape through, for example, a paste-on High-Efficiency Particulate Air (HEPA) filter in the lid. Once the container is full to the point that the HEPA filter is wet with the chemically-treated water, it may be left to soak for a predetermined period of time.

What is claimed is:

1. A sealable decontamination holding vessel for isolating contaminated items, comprising:
   an outer container having an open top and an interior holding chamber;
   an inner receptacle having an open top and an interior confining chamber, the inner receptacle fitting through the open top of the outer container and into the interior holding chamber of the outer container so as to provide a void between the outer container and the inner receptacle;

a cover lid securable and sealable over and upon the open top of the outer container;

at least one vent in at least one of the outer container and the cover lid, wherein the at least one vent has a sealed state and an unsealed state and, when in the unsealed state, allows sterilizing fluid to flow through the vent and into the inner receptacle to contact contaminated items contained in the inner receptacle; and at least one seal patch closing the at least one vent.

2. A sealable decontamination holding vessel for isolating contaminated items, comprising:

an outer container having an open top and an interior holding chamber;

an inner receptacle having an open top and an interior confining chamber, the inner receptacle fitting through the open top of the outer container and into the interior holding chamber of the outer container so as to provide a void between the outer container and the inner receptacle;

wherein the inner receptacle has a plurality of perforations placing the interior confining chamber of the inner receptacle in communication with the void between the outer container and the inner receptacle;

a cover lid securable and sealable over and upon the open top of the outer container; and at least one vent in at least one of the outer container and the cover lid being configured to allow flow of sterilizing fluid through the vents and into the inner receptacle to contact contaminated items contained in the inner receptacle; and at least one seal patch closing the at least one vent, wherein the at least one seal patch is configured to unseal in response to contact with the sterilizing fluid.

3. The sealable decontamination holding vessel of claim 2, further comprising a containment bag having a top open end and an interior collection cavity, the containment bag fitting through the open top of the inner receptacle and into the interior confining chamber of the inner receptacle.

4. The sealable decontamination holding vessel of claim 2, further comprising at least one spacer in the outer container spaced from one another about the interior holding chamber so as to provide the void between the outer container and the inner receptacle.

5. The sealable decontamination holding vessel of claim 2, further comprising a plurality of securement devices configured to secure the cover lid to the outer container.

6. The sealable decontamination holding vessel of claim 2, further comprising an annular gasket of yieldably resilient material positioned on an annular outwardly protruding rim on the open top of the outer container to form an annular seal between the cover lid and the open top of the outer container when the cover lid is secured upon the outer container.

7. The sealable decontamination holding vessel of claim 2, further comprising a probe hole defined through the outer container being configured to receive a probe extendable from exteriorly of the outer container through the probe hole and into the holding chamber of the outer container.

8. The sealable decontamination holding vessel of claim 7, further comprising a probe aperture defined through the inner receptacle and being alignable with the probe hole in the outer container to receive a portion of the probe extendable from exteriorly of the inner receptacle through the probe aperture into the interior holding chamber of the inner receptacle.

9. A sealable decontamination holding vessel for isolating contaminated items, comprising:

an outer container having an open top and an interior holding chamber;

an inner receptacle having an open top and an interior confining chamber, the inner receptacle fitting through the open top of the outer container and into the interior holding chamber of the outer container so as to provide a void between the outer container and the inner receptacle;

a cover lid securable and sealable over and upon the open top of the outer container; and at least one vent in at least one of the outer container and the cover lid being configured to allow flow of sterilizing fluid through the vents and into the inner receptacle to contact contaminated items contained in the inner receptacle;

at least one seal patch closing the at least one vent; and a containment bag having a top open end and an interior collection cavity, the containment bag fitting through the open top of the inner receptacle and into the interior confining chamber of the inner receptacle.

10. The sealable decontamination holding vessel of claim 9, wherein the at least one seal patch is configured to unseal in response to contact with the sterilizing fluid.

* * * * *